United States Patent [19]

Rose et al.

[11] Patent Number: 4,619,666

[45] Date of Patent: Oct. 28, 1986

[54] HAIR DYES CONTAINING AMINO-NITROBENZOIC ACID OR AMINO-NITROBENZENE SULFONIC ACIDS AS SUBSTANTIVE DYES

[75] Inventors: David Rose, Hilden; Edgar Lieske, Duesseldorf; Norbert Maak, Neuss, all of Fed. Rep. of Germany

[73] Assignee: Henkel Kommanditgesellschaft auf Aktien, Duesseldorf, Fed. Rep. of Germany

[21] Appl. No.: 752,889

[22] Filed: Jul. 8, 1985

[30] Foreign Application Priority Data

Jul. 7, 1984 [DE] Fed. Rep. of Germany ....... 3425151

[51] Int. Cl.[4] .................. A61K 7/13; C07C 101/52; C07D 295/08
[52] U.S. Cl. ........................ 8/414; 8/423; 8/649; 260/509; 546/184; 546/232; 562/437; 544/166; 544/167
[58] Field of Search ..................... 8/414, 423

[56] References Cited

U.S. PATENT DOCUMENTS

| | | | |
|---|---|---|---|
| 3,168,442 | 2/1965 | Brunner et al. | 564/423 |
| 4,066,457 | 1/1978 | Panasik et al. | 430/236 |
| 4,189,589 | 2/1980 | Meyer et al. | 548/327 |
| 4,417,896 | 11/1983 | Bugaut et al. | 8/414 |

FOREIGN PATENT DOCUMENTS 2108994  5/1983  United Kingdom ................ 8/415

OTHER PUBLICATIONS

J. Martin et al., J. Chem. Soc. Perkin I, 1974, 2451-2458.
J. F. Corbett in Venkataraman's "the Chemistry of Synthetic Dyes", vol. V (Academic Press), 1971, pp. 508-512.

*Primary Examiner*—A. Lionel Clingman
*Attorney, Agent, or Firm*—Ernest G. Szoke; Henry E. Millson, Jr.

[57] ABSTRACT

Hair coloring preparations containing substantive hair dyes corresponding to the following general formula

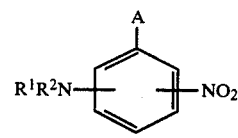

in which A is an $SO_3H$ group or a COOH group, and $R^1$ and $R^2$ are hydrogen or other substituents, show high fastness properties and favorable toxicological properties. The substantive hair dyes are preferably present in the hair coloring preparations in a quantity of from 0.01 to 5.0% by weight, optionally in conjunction with known oxidation hair dye precursors.

15 Claims, No Drawings

HAIR DYES CONTAINING AMINO-NITROBENZOIC ACID OR AMINO-NITROBENZENE SULFONIC ACIDS AS SUBSTANTIVE DYES

BACKGROUND OF THE INVENTION

This invention relates to hair coloring preparations containing substantive hair dyes. Hair coloring preparations of the type in question contain substantive hair dyes in a cosmetic carrier. In addition, they often contain oxidation dye precursors for obtaining certain shades. The cosmetic carriers used for the substantive hair dyes and, optionally, oxidation dye precursors include creams, emulsions, gels, shampoos, foam aerosols and other preparations which are suitable for application to the hair.

In addition to oxidation dyes, which are formed by oxidative coupling of one or more developer components with one another or with one or more coupler components, substantive hair dyes play a particularly important part in the dyeing of hair. The advantage of substantive dyes is that they may be used without the addition of oxidizing agents. The substantive dyes used are primarily compounds belonging to the group of nitrobenzene derivatives. They are used either on their own or in combination with other substantive dyes, such as anthraquinone dyes, indophenols, or with oxidation dyes.

Good hair coloring preparations have to form the required shades with sufficient intensity. They must also be readily absorbed by human hair without excessively staining the scalp. The hair colorings obtained have to be stable to light, heat, perspiration, shampoos and also to the chemicals used in the permanent waving of hair. Finally, they must be safe to use both from the toxicological and from the dermatological viewpoint.

Among substantive nitrobenzene derivatives, nitroanilines and their derivatives occupy a special position because some of these dyes form intensive, light-stable shades. Unfortunately, known substantive nitroaniline dyes are not fast to washing, i.e. they bleed after repeated washing of the hair. In addition, substantive dyes have to be compatible with other dyes, for example with oxidation dye precursors and with the components normally present in oxidation hair dyes, because substantive dyes and oxidation dyes are often used in combination for changing shades. Accordingly, high stability to reducing agents and oxidizing agents is essential.

OBJECTS OF THE INVENTION

An object of the present invention is the development of a hair coloring preparation containing at least one substantive hair dye of the nitroaniline type which is not subject to the drawbacks outlined above.

Another object of the present invention is the development of a hair coloring preparation containing at least one substantive hair dye compound selected from the group consisting of (1) compounds having the formula

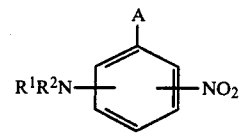

wherein A is an acidic group selected from the group consisting of —$SO_3H$ and —COOH, $R^1$ and $R^2$ each are selected from the group consisting of hydrogen, $C_1$–$C_4$-alkyl, and —$(CH_2)_n$—X, where n is an integer from 2 to 4 and X is a member selected from the group consisting of —OH and —$NR^3R^4$, where $R^3$ and $R^4$ each are selected from the group consisting of hydrogen, $C_1$–$C_4$-alkyl, $C_2$–$C_4$-hydroxyalkyl, and $R^1$ and $R^2$, together with the nitrogen are heterocycles selected from the group consisting of piperidino, pyrrolidino, piperazino and morpholino and (2) water-soluble salts thereof, in an amount sufficient to dye hair as a substantive hair dye.

A further object of the present invention is the development of a method of dyeing human hair employing the above hair coloring preparations.

These and other objects of the invention will become more apparent as the description thereof proceeds.

DESCRIPTION OF THE INVENTION

It has been found that the requirements stated above are satisfied to a high degree by hair coloring preparations containing, as substantive dyes, compounds corresponding to the following general formula I

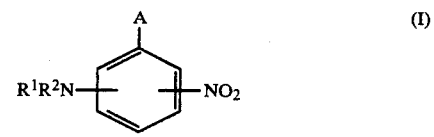 (I)

in which A is an $SO_3H$ or a COOH, $R^1$ and $R^2$ represent hydrogen, a $C_1$–$C_4$ alkyl, a —$(CH_2)_n$—X, where n=2–4 and X is a hydroxyl or -$NR^3R^4$, where $R^3$ and $R^4$ represent hydrogen, a $C_1$–$C_4$ alkyl, a $C_2$–$C_4$ hydroxyalkyl or a $C_2$–$C_4$ aminoalkyl, or $R^1$ and $R^2$ together with the nitrogen atom form a piperidine, pyrrolidine, piperazine or morpholine ring, or water-soluble salts of these compounds.

More particularly, the present invention relates to a hair coloring preparation containing at least one substantive hair dye compound selected from the group consisting of (1) compounds having the formula I

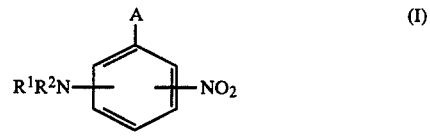 (I)

wherein A is an acidic group selected from the group consisting of —$SO_3H$ and —COOH, $R^1$ and $R^2$ each are selected from the group consisting of hydrogen, $C_1$–$C_4$-alkyl, and —$(CH_2)_n$—X, where n is an integer from 2 to 4 and X is a member selected from the group consisting of —OH and —$NR^3R^4$, where $R^3$ and $R^4$ each are selected from the group consisting of hydrogen, $C_1$–$C_4$-alkyl, $C_2$–$C_4$-hydroxyalkyl, and $R^1$ and $R^2$, together with the nitrogen are heterocycles selected from the group consisting of piperidino, pyrrolidino, piperazino and morpholino and (2) water-soluble salts thereof, in an amount sufficient to dye hair as a substantive hair dye; as well as the process of dyeing human hair employing the above hair coloring preparation.

In the compounds of general formula I, the nitro group and the amino group may be arranged in any position relative to the group A and to one another. The dyes corresponding to general formula I form on the hair highly intense shades of yellow to olive-brown which are fast to light and washing. Compared with known nitroaniline dyes, they show better solubility in aqueous-alkaline medium. The compounds are dermatologically and toxicologically safe.

The compounds corresponding to general formula I are produced by methods known from the literature. In general, they are produced by reaction of the corresponding chloronitrobenzene sulfonic acid or the corresponding chloronitrobenzoic acid with primary or secondary amines in accordance with the following general reaction scheme:

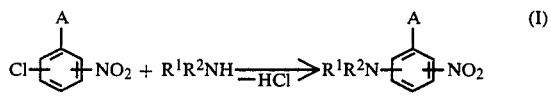

in which the substituents A, $R^1$ and $R^2$ have the same meaning as in formula I. The production of some compounds corresponding to formula I which are not known from the literature is described in the examples hereafter.

Suitable compounds corresponding to general formula I, in which A is an $SO_3H$ group, are for example:
2-amino-3-nitrobenzene sulfonic acid
3-amino-2-nitrobenzene sulfonic acid
4-amino-2-nitrobenzene sulfonic acid
2-amino-4-nitrobenzene sulfonic acid 4-piperidino-3-nitrobenzene sulfonic acid
4-(β-hydroxyethylamino)-3-nitrobenzene sulfonic acid
4-methylamino-3-nitrobenzene sulfonic acid
2-piperidino-5-nitrobenzene sulfonic acid
2-morpholino-5-nitrobenzene sulfonic acid
2-pyrrolidino-5-nitrobenzene sulfonic acid
2-(β-hydroxyethylamino)-5-nitrobenzene
2-bis-(β-hydroxyethyl)-amino-5-nitrobenzene sulfonic acid
2-ethylamino-5-nitrobenzene sulfonic acid
2-dimethylamino-5-nitrobenzene sulfonoc acid
2-piperazino-5-nitrobenzene sulfonic acid Suitable compounds corresponding to formula I, in which A is a COOH group, are for example:
2-amino-4-nitrobenzoic acid
2-methylamino-5-nitrobenzoic acid
2-(β-hydroxyethylamino)-5-nitrobenzoic acid
2-dimethylamino-5-nitrobenzoic acid
2-piperidino-5-nitrobenzoic acid
2-morpholino-5-nitrobenzoic acid
4-amino-3-nitrobenzoic acid
4-diethylamino-3-nitrobenzoic acid
4-methylamino-3-nitrobenzoic acid
4-ethylamino-3-nitrobenzoic acid
4-dimethylamino-3-nitrobenzoic acid
4-morpholino-3-nitrobenzoic acid
4-piperidino-3-nitrobenzoic acid
4-pyrrolidino-3-nitrobenzoic acid
4-(β-hydroxyethylamino)-3-nitrobenzoic acid
3-amino-2-nitrobenzoic acid
2-amino-3-nitrobenzoic acid
2-piperazino-5-nitrobenzoic acid
4-(2-dimethylamino)-ethylamino-3-nitrobenzoic acid
5-amino-2-nitrobenzoic acid Among the compounds corresponding to formula I, in which A is an $SO_3H$ group, 2-piperidino-5-nitrobenzene sulfonic acid and 4(β-hydroxyethyl)-amino-3-nitrobenzene sulfonic acid are particularly preferred substantive hair dyes. Among the compounds corresponding to formula I, in which A is a COOH group, 4-methylamino-3-nitrobenzoic acid, 4-ethylamino-3-nitrobenzoic acid, 2-piperidino-5-nitrobenzoic acid, 5-amino-2-nitrobenzoic acid and 2-amino-4-nitrobenzoic acid are particularly suitable substantive hair dyes.

In the above listing, it is to be understood that the water-soluble salts, particularly the alkali metal salts, such as the sodium salt, are suitable in the same manner as the free acids.

The hair coloring preparations according to the invention may contain the substantive nitroaniline acids of general formula I either on their own or in combination with known substantive dyes, for example with other nitrobenzene derivatives, anthraquinone dyes or azo dyes. In addition, the substantive dyes of general formula I, by virtue of their high resistance to reducing agents and oxidizing agents, are also very suitable for combination with oxidation dye precursors, i.e. for modifying the shades of oxidation hair dyes. Oxidation hair dyes contain as dye precursors developer components which form the oxidation dyes by oxidative coupling with one another or with suitable coupler components. The developer components used are, for example, primary aromatic amines containing another free or substituted hydroxy or amino group in the para or ortho position, diaminopyridine derivatives, heterocyclic hydrazones, 4-aminopyrazolone derivatives and 2,4,5,6-tetraaminopyrimidine and derivatives thereof. The coupler components used include m-phenylene diamine derivatives, naphthols, resorcinol and resorcinol derivatives, pyrazolones and m-aminophenols.

To produce the hair coloring preparations according to the invention, the substantive hair dyes and, optionally, the oxidation dye precursors are incorporated in a suitable cosmetic carrier, for example in creams, emulsions, gels or even surfactant-containing, foaming solutions, for example in shampoos, foam aerosols or other preparations which are suitable for application to hair.

Standard ingredients of cosmetic preparations such as these are, for example, wetting agents and emulsifiers, such as anionic, nonionic or ampholytic tensides (or suface-active compounds), for example fatty alcohol sulfates, alkane sulfonates, α-olefin sulfonates, fatty alcohol polyglycol ether sulfates, ethylene oxide adducts with fatty alcohols, fatty acids and alkyl phenols, sorbitan fatty acid esters and fatty acid partial glycerides, fatty acid alkanolamides and also thickeners such as, for example, methyl or hydroxyethyl cellulose, starch, fatty alcohols, paraffin oils, fatty acids, also perfume oils and hair-care additives such as, for example, water-soluble cationic polymers, protein derivatives, pantothenic acid and cholesterol. The ingredients of the cosmetic carriers are used in the usual quantities in the production of the hair coloring preparations according to the invention. For example, the emulsifiers are used in concentrations of from 0.5 to 30% by weight and the thickeners in concentrations of from 0.1 to 25% by weight, based on the coloring preparation as a whole.

The substantive dyes corresponding to general formula I are used in the hair coloring preparations according to the invention in a quantity of from 0.01 to 5.0% by weight and preferably in a quantity of from 0.1 to 2% by weight, based on the hair coloring preparation as a whole. In addition, known oxidation hair dye precursors (developer and coupler components) may be present in a quantity of from 0.01 to 5% by weight an preferably in a quantity of from 1 to 3% by weight.

If the hair coloring preparation according to the invention contains oxidation dye precursors, it is advisable to add a small quantity of a reducing agent, for example from 0.5 to 2.0% by weight of sodium sulfite, to stabilize the oxidation dye precursors. In this case, an oxidizing agent is added to the hair coloring preparation before it is used in order to initiate the oxidative development of the oxidation dye precursors. Suitable oxidizing agents are, in particular, hydrogen peroxide or adducts thereof with urea, melamine or sodium borate and also mixtures of these hydrogen peroxide adducts with potassium peroxide sulfate.

The hair coloring preparations according to the invention may be used in a mildly acidic, neutral or alkaline medium, irrespective of the cosmetic carrier used, for example a cream, gel or shampoo. The preparations are preferably used in the pH range from about 8 to about 10. They may be used at temperatures of from 15° C. to 40° C. After a contact time of around 30 mins., the preparation is removed by rinsing from the hair to be dyed. The hair is then washed with a mild shampoo and dried. Washing with a shampoo is unnecessary when a carrier of high tenside content, for example a dye shampoo, is used.

Using the hair coloring preparations according to the invention, it is possible to obtain hair colorings characterized by high intensity and good fastness properties and, in particular, by high fastness to washing and by high stability to bleeding and to changes in color on shampooing.

The following Examples are intended to illustrate the invention without limiting it in any way.

EXAMPLES

Example 1

4-($\beta$-hydroxyethyl)-amino-3-nitrobenzene sulfonic acid, Na salt

A mixture of 20 g (0.077 mol) of 4-chloro-3-nitrobenzene sulfonic acid, Na salt, and 9.4 g (0.154 mol) of ethanolamine in 100 ml of water was heated for 6 hours to 120° C.

After the solution had been concentrated by distillation under reduced pressure, the residue was recrystallized from ethanol. A yellow powder melting at 307° C. was obtained.

Example 2

2-($\beta$-hydroxyethyl)-amino-5-nitrobenzene sulfonic acid, Na salt

A mixture of 20 g (0.077 mol) of 2-chloro-5-nitrobenzene sulfonic acid, Na salt, and 9.4 g (0.154 mol) of ethanolamine in 100 ml of water was heated for 6 hours to 120° C.

After the solution had been concentrated by distillation under reduced pressure, the residue was recrystallized from ethanol. A yellow powder melting at 254° C. was obtained.

Example 3

2-bis-($\beta$-hydroxyethyl)-amino-5-nitrobenzene sulfonic acid, acid, Na salt

The procedure was as in Example 2 using 20 g of diethanolamine. A yellow powder melting above 305° C. was obtained.

Example 4

2-ethylamino-5-nitrobenzene sulfonic acid, Na salt

The procedure was as in Example 2 using 30 g of ethylamine. A yellow powder melting at 245° C. was obtained.

Example 5

2-($\beta$-hydroxyethyl)-amino-5-nitrobenzoic acid

A mixture of 10.1 g (0.05 mol) of 2-chloro-5-nitrobenzoic acid, 6 ml (0.1 mol) of ethanolamine and 50 ml of water was heated for 7 hours to 170° C.

After cooling to +10° C., the deposit was filtered off and recrystallized from ethanol. A yellow powder melting at 139° C. was obtained.

Example 6

4-(2-dimethylaminoethyl)-amino-3-nitrobenzoic acid

The procedure was as in Example 5 using 10.1 g (0.05 mol) of 4-chloro-3-nitrobenzoic acid and 20 g (0.15 mol) of N,N-dimethylethylene diamine. A yellow powder melting at 281° C. (with decomposition) was obtained.

The above compounds can readily be obtained in their free acid form or in the form of their alkali metal salts as is well known in the art.

Example 7

Hair Dyeing Tests

Hair dyeing creams having the following composition were prepared:

| | |
|---|---|
| $C_{12}$–$C_{18}$ fatty alcohol | 10 g |
| $C_{12}$–$C_{14}$ fatty alcohol + 2 EO sulfate, Na salt (28%) | 25 g |
| Water | 60 g |
| Substantive dye | 1 g |
| Ammonium sulfate | 1 g |
| Concentrated ammonia solution | to pH = 9.5 |
| Water | ad 100 g |

The constituents were mixed together in the above order. After addition of the substantive dyes, the pH value of the emulsion was adjusted to 9.5 with concentrated ammonia solution, after which the emulsion was made up with wate to 100 g.

The dyeing cream was applied to approx. 5 cm long strands of standardized, 90% gray, but not specially pretreated human hair and left thereon for 30 minutes at 27° C. After dyeing, the hair was rinsed, washed with a standard shampoo and then dried.

The following compounds were used as the substantive hair dyes:

| | |
|---|---|
| 7.1 | 2-piperidino-5-nitrobenzene sulfonic acid |
| 7.2 | 4-($\beta$-hydroxyethyl)-amino-3-nitrobenzene sulfonic acid, Na salt |
| 7.3 | 4-dimethylamino-3-nitrobenzene sulfonic acid, Na salt |
| 7.4 | 4-piperidino-3-nitrobenzene sulfonic acid, Na |

-continued

| | |
|---|---|
| 7.5 | 2-morpholino-5-nitrobenzene sulfonic acid, Na salt |
| 7.6 | 2-dimethylamino-5-nitrobenzene sulfonic acid, Na salt |
| 7.7 | 2-ethylamino-5-nitrobenzene sulfonic acid, Na salt |
| 7.8 | 2-bis-(β-hydroxyethyl)-amino-5-nitrobenzene sulfonic acid, Na salt |
| 7.9 | 2-(β-hydroxyethyl)-amino-5-nitrobenzene sulfonic acid, Na salt |
| 7.10 | 2-pyrrolidino-5-nitrobenzene sulfonic acid, Na salt |
| 7.11 | 2-amino-5-nitrobenzene sulfonic acid |
| 7.12 | 4-amino-2-nitrobenzene sulfonic acid |
| 7.13 | 2-amino-4-nitrobenzoic acid |
| 7.14 | 4-methylamino-3-nitrobenzoic acid |
| 7.15 | 4-ethylamino-3-nitrobenzoic acid |
| 7.16 | 2-(β-hydroxyethyl)-amino-5-nitrobenzoic acid |
| 7.17 | 2-dimethylamino-5-nitrobenzoic acid |
| 7.18 | 2-piperdino-5-nitrobenzoic acid |
| 7.19 | 4-dimethylamino-3-nitrobenzoic acid |
| 7.20 | 2-methylamino-5-nitrobenzoic acid |
| 7.21 | 2-morpholino-5-nitrobenzoic acid |
| 7.22 | 2-pyrrolidino-5-nitrobenzoic acid |
| 7.23 | 4-(2-dimethylaminoethyl)-amino-3-nitrobenzoic acid |
| 7.24 | 2-dimethylamino-5-nitrobenzoic acid |
| 7.25 | 4-pyrrolidino-3-nitrobenzoic acid |
| 7.26 | 4-morpholino-3-nitrobenzoic acid |
| 7.27 | 4-piperidino-3-nitrobenzoic acid |
| 7.28 | 4-dimethylamino-3-nitrobenzoic acid |

The results of the dyeing tests are shown in Table I.

TABLE I

| Substantive dye | Shade |
|---|---|
| 7.1 | olive-yellow |
| 7.2 | olive-brown |
| 7.3 | honey-yellow |
| 7.4 | clay-colored |
| 7.5 | olive |
| 7.6 | olive-yellow |
| 7.7 | olive-yellow |
| 7.8 | khaki |
| 7.9 | olive |
| 7.10 | olive-yellow |
| 7.11 | olive-yellow |
| 7.12 | beige |
| 7.13 | yellow |
| 7.14 | olive-brown |
| 7.15 | honey-yellow |
| 7.16 | olive-yellow |
| 7.17 | khaki |
| 7.18 | khaki |
| 7.19 | clay-colored |
| 7.20 | olive-yellow |
| 7.21 | khaki |
| 7.22 | olive |
| 7.23 | khaki |
| 7.24 | olive-yellow |
| 7.25 | olive-brown |
| 7.26 | gray-yellow |
| 7.27 | dark blond |
| 7.28 | olive-brown |

As can be seen in Table I, all the compounds tested gave light shades without presence of the oxidative dye precursors.

The substantive dyes oF example 7.1, 7.2, 7.13, 7.14, 7.15 and 7.18 are preferred for their superior stability to light, heat and shampooing.

The preceding specific embodiments are illustrative of the practice of the invention. It is to be understood however, that other expedients known to the skilled in the art or disclosed herein may be employed without departing from the spirit of the invention or the scope of the appended claims.

What is claimed:

1. A hair coloring preparation containing at least one substantive hair dye compound selected from the group consisting of (1) compounds having the formula

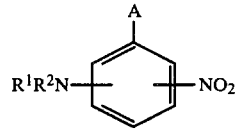

wherein A is an acidic group selected from the group consisting of —SO$_3$H and —COOH, R$^1$ and R$^2$ each are selected from the group consisting of hydrogen, C$_1$–C$_4$-alkyl, and —(CH$_2$)$_n$—X, where n is an integer from 2 to 4 and X is, a member selected from the group consisting of —OH and —NR$^3$R$^4$, where R$^3$ and R$^4$ each are selected from the group consisting of hydrogen, C$_1$–C$_4$-alkyl, C$_2$–C$_4$-hydroxyalkyl, and R$^1$ and R$^2$, together with the nitrogen are heterocycles selected from the group consisting of piperidino, pyrrolidino, piperazino and morpholino and (2) water-soluble salts thereof, in an amount sufficient to dye hair as a substantive hair dye.

2. The hair coloring preparation of claim 1 wherein at least one compound from the group consisting of 2-piperidino-5-nitrobenzene sulfonic acid and 4-(β-hydroxyethyl)-amino-3-nitrobenzene sulfonic acid or a water soluble salt thereof is present as the substantive dye.

3. The hair coloring preparation of claim 1 wherein at least one compound from the group consisting of 4-methylamino-3-nitrobenzoic acid, 4-ethylamino-3-nitrobenzoic acid, 2-piperidino-5-nitrobenzoic acid and 2-amino-4-nitrobenzoic acid or a water-soluble salt thereof is present as the substantive dye.

4. The hair coloring preparation of claim 1 wherein said amount sufficient to dye hair of said substantive hair dye compound is from 0.01% to 5% by weight, based on the hair coloring preparation as a whole.

5. The hair coloring preparation of claim 4 wherein said amount is from 0.1% to 2% by weight.

6. The hair coloring preparation of claim 2 wherein said amount sufficient to dye hair of said substantive hair dye compound is from 0.01% to 5% by weight, based on the hair coloring preparation as a whole.

7. The hair coloring preparation of claim 6 wherein said amount is from 0.1% to 2% by weight.

8. The hair coloring preparation of claim 3 wherein said amount sufficient to dye hair of said substantive hair dye compound is from 0.01% to 5% by weight, based on the hair coloring preparation as a whole.

9. The hair coloring preparation of claim 8 wherein said amount is from 0.1% to 2% by weight.

10. The hair coloring preparation of claim 1 wherein known oxidation hair dye precursors are additionally present in an amount of from 0.01% to 5% by weight, based on the hair coloring preparation as a whole.

11. The hair coloring preparation of claim 10 wherein said oxidation hair dye precursors are present in an amount of from 1% to 3% by weight.

12. A method for the dyeing of human hair comprising applying to said hair, at temperatures ranging from about 15° to 40° C. for a time sufficient to effect dyeing an effective amount of the hair coloring preparation of claim 1.

13. The method of claim 12 wherein the pH of the hair coloring preparation is controlled between abut 8 and about 10.

14. The hair coloring preparation of claim 1 which comprises
  (1) from about 0.01% to 5% by weight of said at least one substantive hair dye compound
  (2) from about 0.5% to 30% by weight of an anionic or nonionic or ampholytic wetting and emulsifying agent;
  (3) from about 0.1% to 25% by weight of thickeners; and
  (4) the balance water.

15. A process for the dyeing of human hair comprising applying to said hair, at temperatures ranging substantially from about 15° to 40° C. at a pH of from about 8 to 10 for a time sufficient to effect dyeing an effective amount of the composition of claim 14.

* * * * *